(12) United States Patent
Birnkrant et al.

(10) Patent No.: US 10,524,643 B2
(45) Date of Patent: Jan. 7, 2020

(54) IMAGE SENSOR MODULE WITH TURNING PRISM

(71) Applicant: KARL STORZ Endovision, Inc., Charlton, MA (US)

(72) Inventors: Dashiell Birnkrant, Sutton, MA (US); Naushad Kasim, Southbridge, MA (US); Margus Lohk, Harjumaa (EE); Indrek-Toomas Polluks, Virumaa (EE)

(73) Assignee: KARL STORZ Endovision, Inc., Charlton, MA (US)

( * ) Notice: Subject to any disclaimer, the term of this patent is extended or adjusted under 35 U.S.C. 154(b) by 171 days.

(21) Appl. No.: 15/804,261

(22) Filed: Nov. 6, 2017

(65) Prior Publication Data
US 2019/0133423 A1    May 9, 2019

(51) Int. Cl.
| | |
|---|---|
| *A61B 1/04* | (2006.01) |
| *G01J 1/02* | (2006.01) |
| *G01J 1/04* | (2006.01) |
| *G01J 1/42* | (2006.01) |
| *A61B 1/00* | (2006.01) |

(52) U.S. Cl.
CPC .............. *A61B 1/04* (2013.01); *G01J 1/0271* (2013.01); *G01J 1/0477* (2013.01); *G01J 1/42* (2013.01); *A61B 1/00188* (2013.01)

(58) Field of Classification Search
CPC .. A61B 1/04; A61B 1/05; A61B 1/051; A61B 1/053; A61B 1/00064; A61B 1/00071; A61B 1/0008; A61B 1/00096; A61B 1/00098; A61B 1/00101; A61B 1/00188; A61B 1/00163; A61B 1/0011; G01J 1/0271; G01J 1/0477; G01J 1/42; H04N 5/225; H04N 5/2251; H04N 5/22521; H04N 2005/2255; H04N 5/2252; H04N 5/2257; H04N 5/2254
See application file for complete search history.

(56) References Cited

U.S. PATENT DOCUMENTS

| | | | | |
|---|---|---|---|---|
| 4,646,721 | A | * | 3/1987 | Arakawa ................... A61B 1/05 600/130 |
| 4,741,327 | A | | 5/1988 | Yabe |
| 5,220,198 | A | * | 6/1993 | Tsuji ......................... A61B 1/05 257/680 |
| 5,365,268 | A | * | 11/1994 | Minami .................... A61B 1/05 257/E31.118 |

(Continued)

*Primary Examiner* — John R Lee
(74) *Attorney, Agent, or Firm* — Michael Joseph Loi; David Noel Villalpando (57) ABSTRACT

An image sensor module includes a circuit board, an image sensor, and a turning prism. The circuit board has first and second side sections each extending in a respective plane transverse to a plane of a center section to define a module interior volume. The image sensor has a bottom plane mounted on an inner face of the circuit board within the module interior volume. The turning prism has a mounting surface secured to a top plane of the image sensor. An electronic component arrangement is operatively mounted on the inner face of the circuit board between the image sensor and a circuit board rearward end. A number of wires providing power and data connections to the circuit board are operatively connected to contacts located on the circuit board in the interior volume between the electronic component arrangement and the circuit board rearward end.

20 Claims, 8 Drawing Sheets

(56) References Cited

U.S. PATENT DOCUMENTS

| | | | |
|---|---|---|---|
| 5,427,087 A * | 6/1995 | Ito | A61B 1/00096 600/109 |
| 5,454,366 A | 10/1995 | Ito | |
| 5,734,418 A * | 3/1998 | Danna | A61B 1/05 348/65 |
| 5,876,326 A * | 3/1999 | Takamura | A61B 1/00124 600/110 |
| 6,313,456 B1 * | 11/2001 | Miyashita | H01L 27/14618 250/208.1 |
| 6,582,360 B1 * | 6/2003 | Torii | A61B 1/018 600/127 |
| 6,605,035 B2 * | 8/2003 | Ando | A61B 1/0008 600/127 |
| 6,956,610 B1 * | 10/2005 | Walls | H04N 5/2252 348/337 |
| 8,698,887 B2 * | 4/2014 | Makino | H04N 5/2254 348/76 |
| 8,814,779 B2 | 8/2014 | Shafer | |
| 9,462,933 B2 | 10/2016 | Ishikawa | |
| 9,474,439 B2 * | 10/2016 | Baumann | A61B 1/00096 |
| 9,554,692 B2 | 1/2017 | Levy | |
| 9,565,997 B2 | 2/2017 | Scott | |
| 2001/0044571 A1 * | 11/2001 | Mitsumori | A61B 1/05 600/167 |
| 2002/0080233 A1 * | 6/2002 | Irion | H04N 5/2251 348/65 |
| 2005/0267328 A1 * | 12/2005 | Blumzvig | A61B 1/00096 600/109 |
| 2007/0282165 A1 * | 12/2007 | Hopkins | A61B 1/00029 600/109 |
| 2011/0249106 A1 * | 10/2011 | Makino | H04N 5/2254 348/76 |
| 2014/0078280 A1 * | 3/2014 | Yoshida | A61B 1/00163 348/76 |
| 2014/0210976 A1 * | 7/2014 | Lin | A61B 1/0011 348/68 |
| 2014/0309491 A1 * | 10/2014 | Karasawa | A61B 1/00124 600/103 |
| 2015/0018619 A1 * | 1/2015 | Adler | H01L 27/14636 600/112 |
| 2015/0318924 A1 * | 11/2015 | Motohara | G02B 6/4259 398/200 |
| 2015/0358519 A1 * | 12/2015 | Kamei | H04N 5/2254 348/68 |
| 2016/0037027 A1 * | 2/2016 | Elliott, Jr. | H04N 5/2252 348/76 |
| 2016/0213229 A1 * | 7/2016 | Kitano | A61B 1/00096 |
| 2016/0213236 A1 * | 7/2016 | Hruska | A61B 1/267 |
| 2016/0345805 A1 * | 12/2016 | Wieters | A61B 1/00096 |
| 2017/0108691 A1 * | 4/2017 | Kitano | A61B 1/051 |
| 2017/0108692 A1 * | 4/2017 | Kitano | G02B 23/2469 |
| 2017/0245744 A1 * | 8/2017 | McDowall | A61B 1/00009 |
| 2017/0265721 A1 * | 9/2017 | Ichimura | A61B 1/04 |
| 2017/0318205 A1 * | 11/2017 | Duckett, III | G02B 23/26 |
| 2017/0325671 A1 * | 11/2017 | Hopkins, Jr. | A61B 1/045 |
| 2018/0070803 A1 * | 3/2018 | Mikami | G02B 23/2423 |
| 2019/0133423 A1 * | 5/2019 | Birnkrant | A61B 1/04 |

\* cited by examiner

IMAGE SENSOR MODULE WITH TURNING PRISM

TECHNICAL FIELD OF THE INVENTION

The invention relates to imaging systems for use in observation instruments such as endoscopes. More particularly, the invention encompasses image sensor modules having configurations which facilitate reduced cross-sectional dimensions at the observation instrument distal head. The invention also encompasses observation instruments and instrument components which incorporate such image sensor modules.

BACKGROUND OF THE INVENTION

Observation instruments such as endoscopes are used in medical and other applications to allow a visual inspection of locations which are not readily accessible. For example, endoscopes are used in medical applications to provide a view of an area within a patient's body. An endoscope typically includes an elongated shaft of relatively small diameter extending from a handle to a distal end. An imaging or viewing arrangement is included with the endoscope to allow a user to obtain a view from the distal end. Particularly in early endoscopes this arrangement included a system of lenses and a light conduit through the shaft to direct an image from the distal end to an eyepiece associated with the endoscope handle. In many modern endoscopes, the imaging or viewing arrangement includes an electronic imaging device mounted in a distal head at the distal end of the endoscope. Such an electronic imaging device collects image data and communicates that data through the shaft and handle ultimately to a processing system that assembles the data into an image to be displayed on a suitable display device.

To provide the desired illumination for the image to be collected, light may be generated by a light source at the endoscope handle and directed through suitable conduits in the shaft (such as optical fibers for example) to the endoscope distal head where the light can be directed as desired through suitable lenses. Alternatively to relying on light conducted through the shaft to the distal end of the endoscope, a suitable light source such as an LED lamp may be placed at the distal head of the endoscope together with the electronic imaging device to provide the required illumination.

In addition to the imaging or viewing arrangement and the illumination arrangement, some endoscopes and similar instruments include a working channel which extends from the instrument handle through the elongated shaft to the distal head. This working channel comprises a passageway through which fluids may be introduced into the area under observation during the endoscopic procedure, or through which a suction may be applied. The working channel may also be used to insert tools into the area under observation for performing certain functions in the course of the endoscopic procedure.

Although it is desirable or necessary to provide room in the distal head of the observation instrument for the imaging or viewing arrangement, illumination arrangement, and working channel, the distal head of the instrument must have a cross-sectional dimension that remains as small as possible in order to facilitate the desired observation and other procedures intended for the instrument. This is true for all applications, but especially for medical applications. This requirement for a small cross-sectional dimension limits the electronic imaging devices which may be used in an observation instrument. In particular, some image sensors are too wide to orient with their image collecting surface parallel to the end of the distal head where the image is to be collected.

U.S. Pat. Nos. 4,741,327 and 5,454,366 each show an endoscope with an imaging device oriented in a plane essentially parallel to the longitudinal axis of the endoscope head. In each case a prism is employed to direct the image from the objective lenses of the device to the imaging device. However, the configurations shown in these two patents are relatively long, leave less room for other components of the distal head, and have other disadvantages.

There remains a need for image sensor arrangements which can be mounted at the distal head of an observation instrument such as an endoscopic device without taking up too much room or requiring a larger distal head.

SUMMARY OF THE INVENTION

It is an object of the invention to provide an image sensor module configured to facilitate a reduced cross-sectional dimension. The reduced cross-sectional dimension allows a corresponding reduction in the cross-sectional dimension of the distal head of an observation instrument such as an endoscope which incorporates the image sensor module. Alternatively or additionally, the reduced cross-sectional dimension of the image sensor module provides more room in the distal head for other elements such as illumination elements and one or more working channels. Aspects of the invention encompass image sensor modules, observation instrument distal heads, and observation instruments.

An image sensor module according to a first aspect of the present invention includes a circuit board, an image sensor mounted on the circuit board, and a turning prism mounted on the image sensor. The circuit board has a center section together with first and second side sections each extending in a respective plane transverse to a plane of the center section to define a module interior volume there between. This module interior volume extends from a forward end of the circuit board and a rearward end of the circuit board. The image sensor has a bottom plane mounted on an inner face of the circuit board within the module interior volume. The turning prism has a mounting surface secured to a top plane of the image sensor also within the module interior volume, with an image receiving surface of the turning prism facing in a direction from the rearward end of the circuit board to the forward end of the circuit board. An electronic component arrangement is also included in the image sensor module operatively mounted on the inner face of the circuit board between the image sensor and the rearward end of the circuit board. The image sensor module further includes a cable assembly having a number of wires entering the module interior volume at the rearward end of the circuit board. These wires are operatively connected to contacts located on the circuit board in the center section, first side section, and second side section between the electronic component arrangement and the rearward end of the circuit board.

The arrangement of components in a module according to this aspect of the invention places the plane of the image sensor essentially parallel to the axis along which the image is captured. This orientation of the image sensor causes it to take up less of the total cross-sectional area of the image sensor module. Also, the position of the cable connection pads between the electronic component arrangement and rearward end of the circuit board allows the cable wires to be connected without adding to the cross sectional dimension of the image sensor module.

According to another aspect of the invention, a distal head for an observation instrument includes a distal head body having an image sensor receiving cavity. An image sensor module according to the first aspect of the invention is mounted in the image sensor receiving cavity so that the turning prism image receiving surface faces in a direction toward an outer end of the distal head body in position to receive an image from that end of the distal head body.

According to a further aspect of the invention, a distal head assembly according to the second aspect described in the previous paragraph is combined with an observation instrument including an instrument handle and elongated shaft. The distal head is connected to a distal end of the elongated shaft so that the outer end of the distal head faces away from the elongated shaft to position the turning prism appropriately for collecting the desired image.

In implementations of an image sensor module according to any of the foregoing aspects of the invention, the first side section of the circuit board and the second side section of the circuit board may each extend approximately perpendicular to the plane of the center section of the circuit board to define the module interior volume. In this arrangement the two side sections of the circuit board extend along the lateral sides of the image sensor and the turning prism. In order to accommodate the position of the circuit board side sections according to these implementations, the circuit board may be flexible along its entire length and width, or at least in interface areas between the different sections.

In implementations of an image sensor module according to any of the foregoing aspects of the invention, the module may include integrated RF shielding. The RF shielding may include an RF shield housing extending at least from the forward end of the circuit board to the rearward end of the circuit board so as to enclose the circuit board along its entire length. A first end of the RF shield housing may be connected to a prism carrier for the turning prism while the opposite second end of the RF shield housing may be connected to an end cap. The end cap may itself comprise an RF shielding material which is sealed to the second end of the RF shield housing. The end cap may in turn be electrically coupled to a shielding layer of the cable assembly for the module. This RF shielding arrangement provides complete RF shielding from RF emitting devices which may be operating in close proximity to the image sensor module and might otherwise interfere with the operation of the module.

In implementations in which the image sensor module is mounted in the distal head of an observation instrument, the module may be mounted in the distal head so that the image sensor is relatively near the outer extent of the distal head. In particular the image sensor module may be mounted in the distal head so that an outer face of the circuit board in the center section lies closer to an outer surface of the distal head than to a central longitudinal axis of the distal head. This configuration leaves more room within the distal head for other components that may be included there.

These and other advantages and features of the invention will be apparent from the following description of representative embodiments, considered along with the accompanying drawings.

DESCRIPTION OF REPRESENTATIVE EMBODIMENTS

Image sensor modules and devices incorporating image sensor modules within the scope of the present invention will be described below primarily with reference to applications in an endoscope. This reference to an endoscope is intended merely as a representative example application and is not intended to be limiting. Implementations may include other observation instruments including optical scopes such as exoscopes and borescopes in addition to endoscopes.

Figure 1:
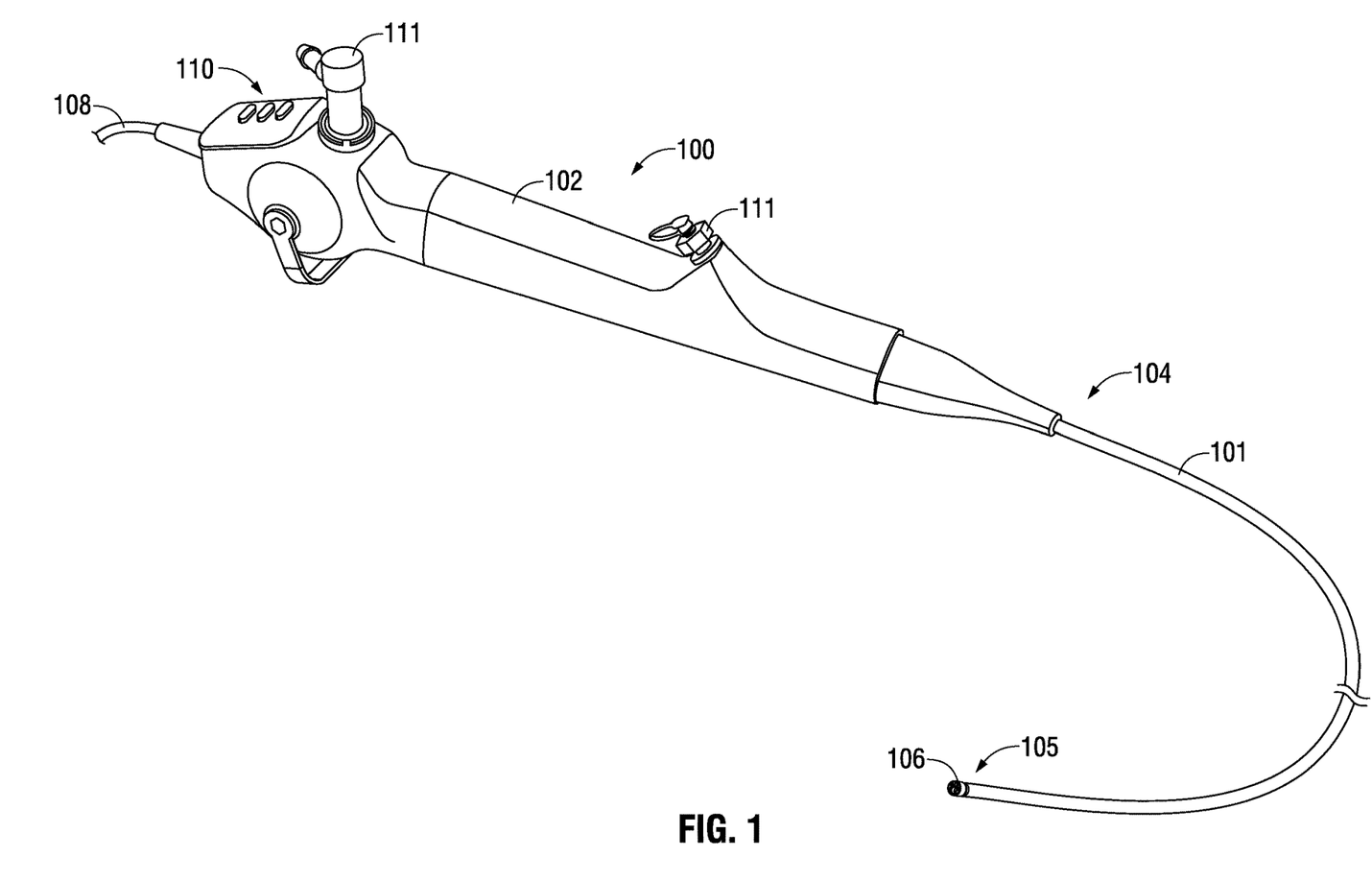
FIG. 1 is a view in perspective of an endoscope including an image sensor module according to an embodiment of the present invention.

Referring to FIG. 1, an endoscope 100 according to one aspect of the present invention includes an elongated shaft 101 and a handle 102. Shaft 101 extends from a proximal end shown generally at reference numeral 104 connected to handle 102 to a distal end generally indicated at reference numeral 105. A distal head 106 is mounted to the shaft distal end 105 and includes an image sensor module according to an aspect of the present invention. The image sensor module and details of distal head 106 are not shown in FIG. 1 due to the scale of the figure but will be described in detail below, particularly with reference to FIGS. 2-8.

Endoscope 100 receives electrical operating power through a cable 108 which extends from a proximal end of handle 102 in this example endoscope. This power may be used to operate the image sensor module associated with distal head 106 and other electronic elements associated with the distal head, such as illumination devices which may be located in that assembly. Also, data signals from the image sensor module in distal head 106 may be communicated through appropriate pathways within shaft 101 and handle 102 to cable 108. In particular, cable 108 (or another cable connected to cable 108) including a suitable number of electrical wires may extend from handle 102 through shaft 101 to the electronic components contained within distal head 106, especially an image sensor module as will be described below. Data signals from the image sensor module may be communicated through cable 108 to processing equipment (not shown) which processes the image data and drives one or more video monitors to display the images collected at distal head 106.

Those familiar with endoscopic systems will appreciate that endoscope 100 includes a number of features such as controls 110 for controlling the operation of the endoscope and ports 111 for introducing fluids or applying a suction to a working channel included in the endoscope. These additional features and the general operation and control of endoscope 100 will not be described further herein in order to avoid obscuring the present invention in unnecessary detail.

Figure 2:
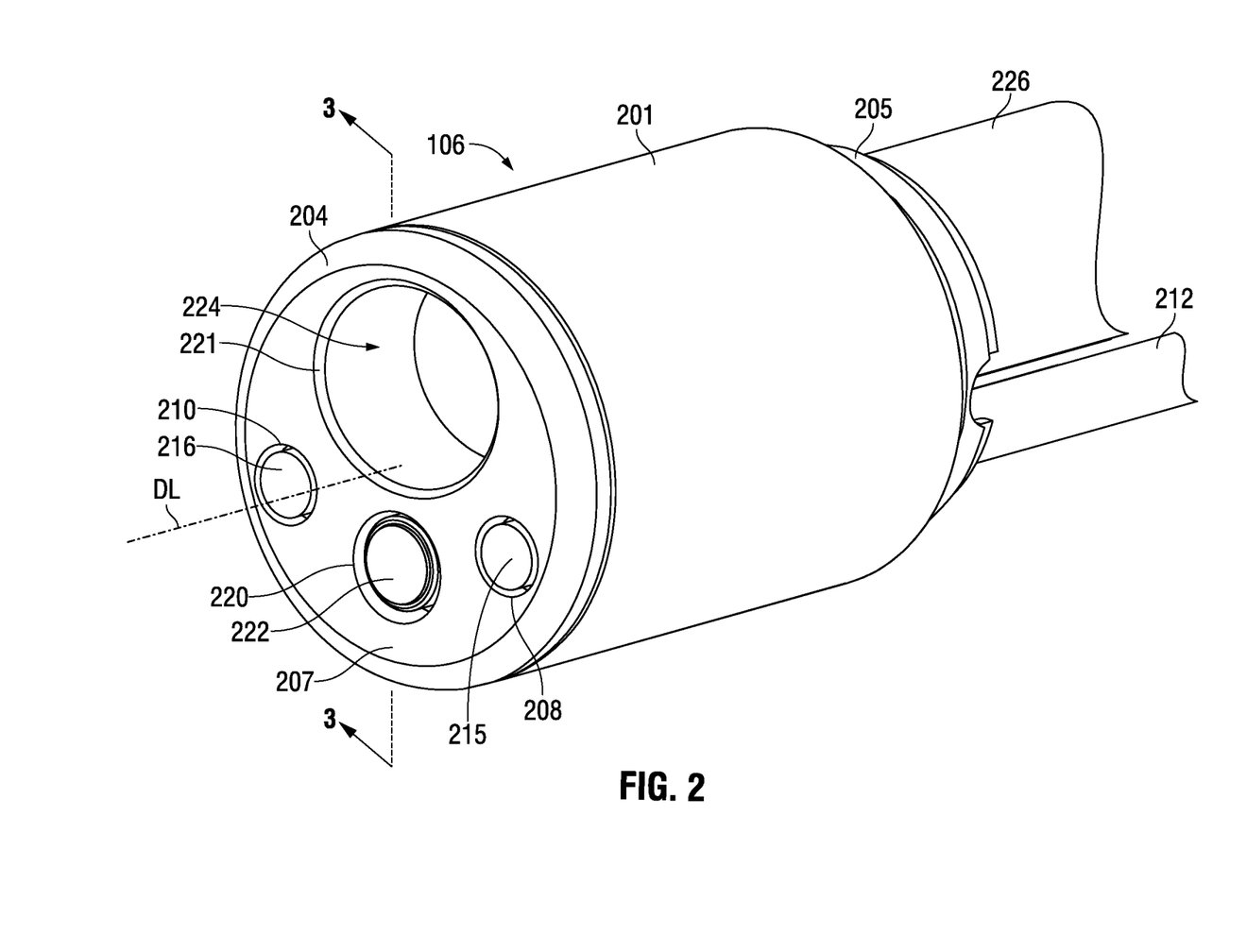
FIG. 2 is a front perspective view of the distal head of the endoscope shown in FIG. 1.
Figure 3:
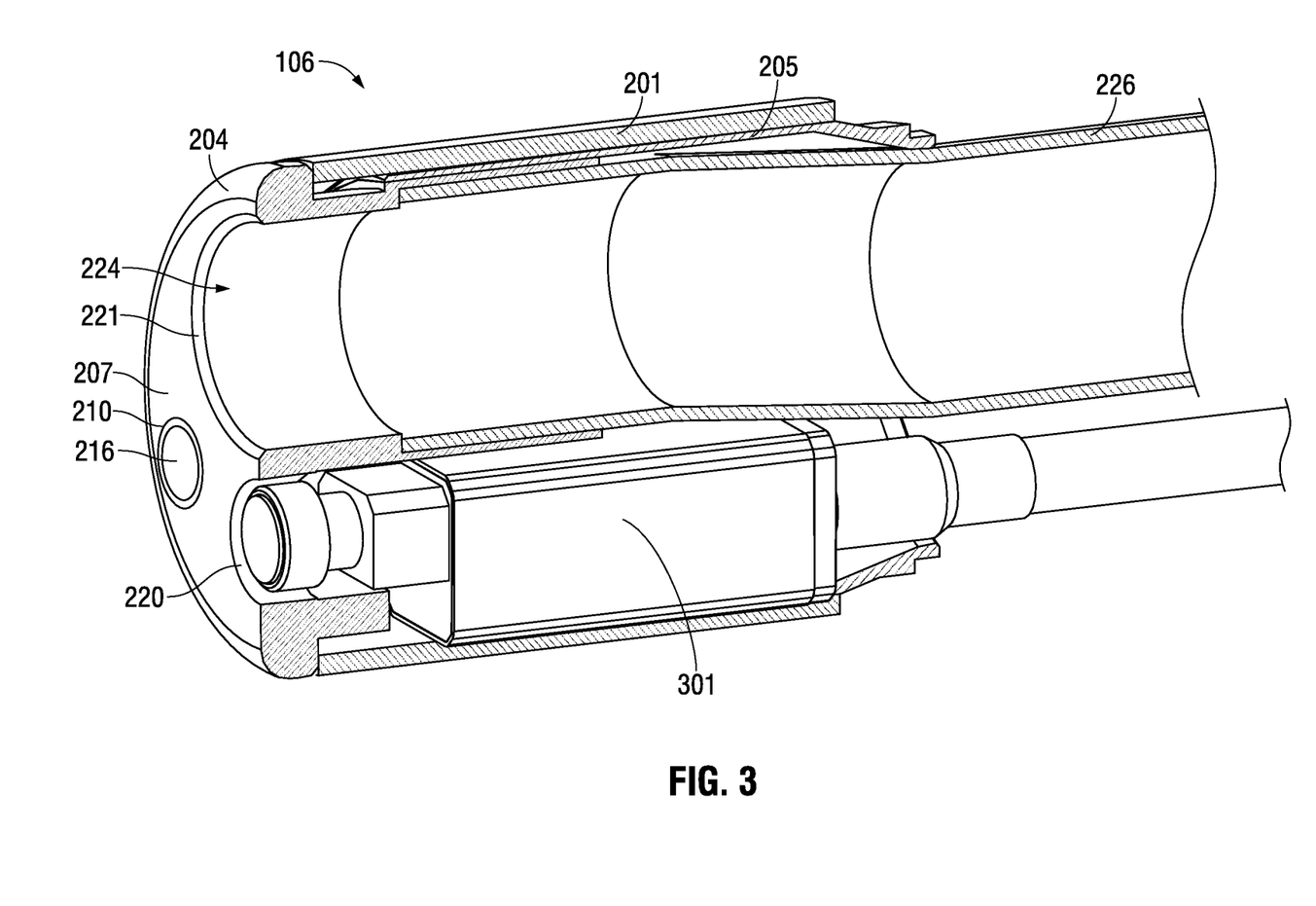
FIG. 3 is a perspective view similar to FIG. 2, but with the distal head shown in longitudinal section along line 3-3 to expose the image sensor module therein.

FIG. 2 shows distal head 106 separated from shaft 101 shown in FIG. 1. The partial section view of FIG. 3 shows distal head 106 in section taken along line 3-3 in FIG. 2, but with the image sensor module 301 intact. In this representative embodiment, distal head 106 comprises a distal head body made up of a cover 201, a distal end section 204, and, as best shown in the section view of FIG. 3, a sleeve 205. An inner end of sleeve 205 (to the right in the orientation of FIGS. 2 and 3) is adapted to be connected to the shaft 101 shown in FIG. 1. In this example implementation, distal head 106 is generally cylindrical in shape and extends along a central longitudinal axis labeled DL in FIG. 2.

As best shown in FIG. 2, distal end section 204 terminates in an outer surface 207 that includes a number of openings for the various components mounted in or terminating in distal head 106. In particular, outer surface 207 of distal end section 204 includes openings 208 and 210 which each lead to a respective cavity in the distal head for receiving a respective illumination device. These cavities are not visible in the views of FIGS. 2 and 3, however a portion of the illumination device leading to the cavity terminating in opening 208 is shown in FIG. 2 as a light guide 212. FIG. 2 also shows a lens or lens cover 215 for light guide 212, and a similar lens or lens cover 216 is shown in opening 210. Although not shown in these views, it will be appreciated that an additional illumination device extends into the cavity associated with opening 210 and terminates at lens or lens cover 216. Surface 207 of distal end section 204 also includes an opening 220 and an opening 221. Opening 220 leads to an image sensor module cavity which will be described below in connection with FIG. 4. Only an outer lens 222 associated with the image sensor module is visible in the perspective of FIG. 2. Opening 221 leads to a cavity shown by arrow 224 which comprises the end of a working channel. FIGS. 2 and 3 both show a portion of a working channel conduit 226 which, when distal head 106 is connected to shaft 101 as shown in FIG. 1, ultimately extends the length of the shaft to handle 102 shown in that figure.

Figure 4:
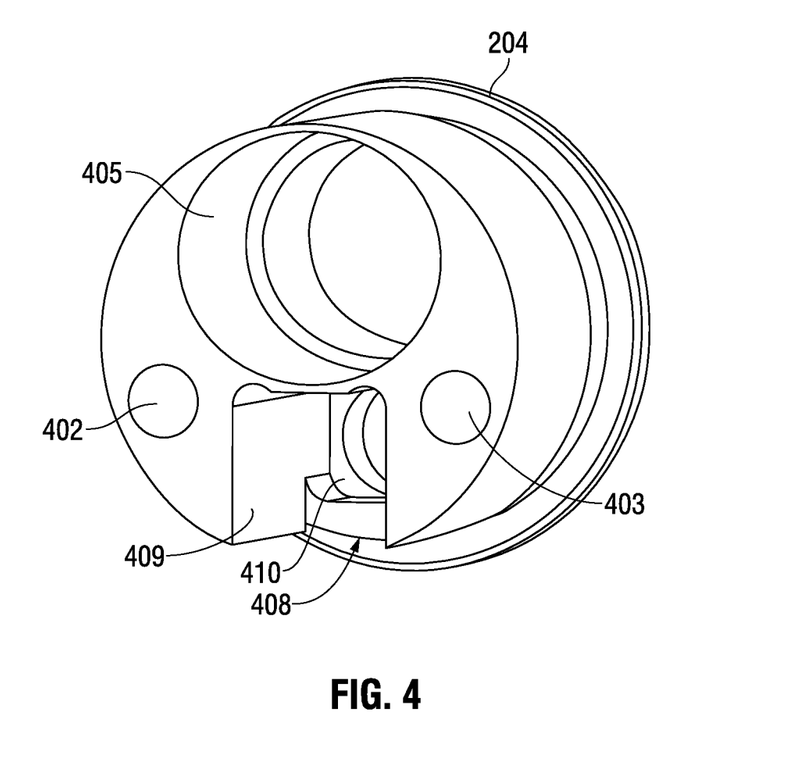
FIG. 4 is a view in perspective of the distal end section of the distal head shown in FIG. 3, shown from the opposite perspective to that shown in FIG. 3.

The perspective of FIG. 4 shows the opposite end of distal end section 204 with the other components making up the distal head body (namely, cover 201 and sleeve 205 from FIGS. 2 and 3) removed. This perspective shows portions of the various cavities of the distal head body. In particular, FIG. 4 shows illumination device cavity 402 for receiving light guide 212 shown in FIG. 2, and illumination device cavity 403 for receiving a second light guide. A cavity 405 is also visible in FIG. 4 for receiving the working channel conduit (226 in FIGS. 2 and 3). FIG. 4 further shows an image sensor module receiving cavity indicated generally at arrow 408. Cavity 408 includes a slot portion 409 and an end section 410. As is apparent from comparing the partial section view of FIG. 3 to FIG. 4, slot portion 409 is sized to receive the main body of image sensor module 301 shown in FIG. 3, and end section 410 is sized to receive a portion of the image sensor module protruding from the image sensor main body. This configuration of distal head section 204 dictates a desired orientation of image sensor module 301 in the distal head as will be described further below.

Figure 5:
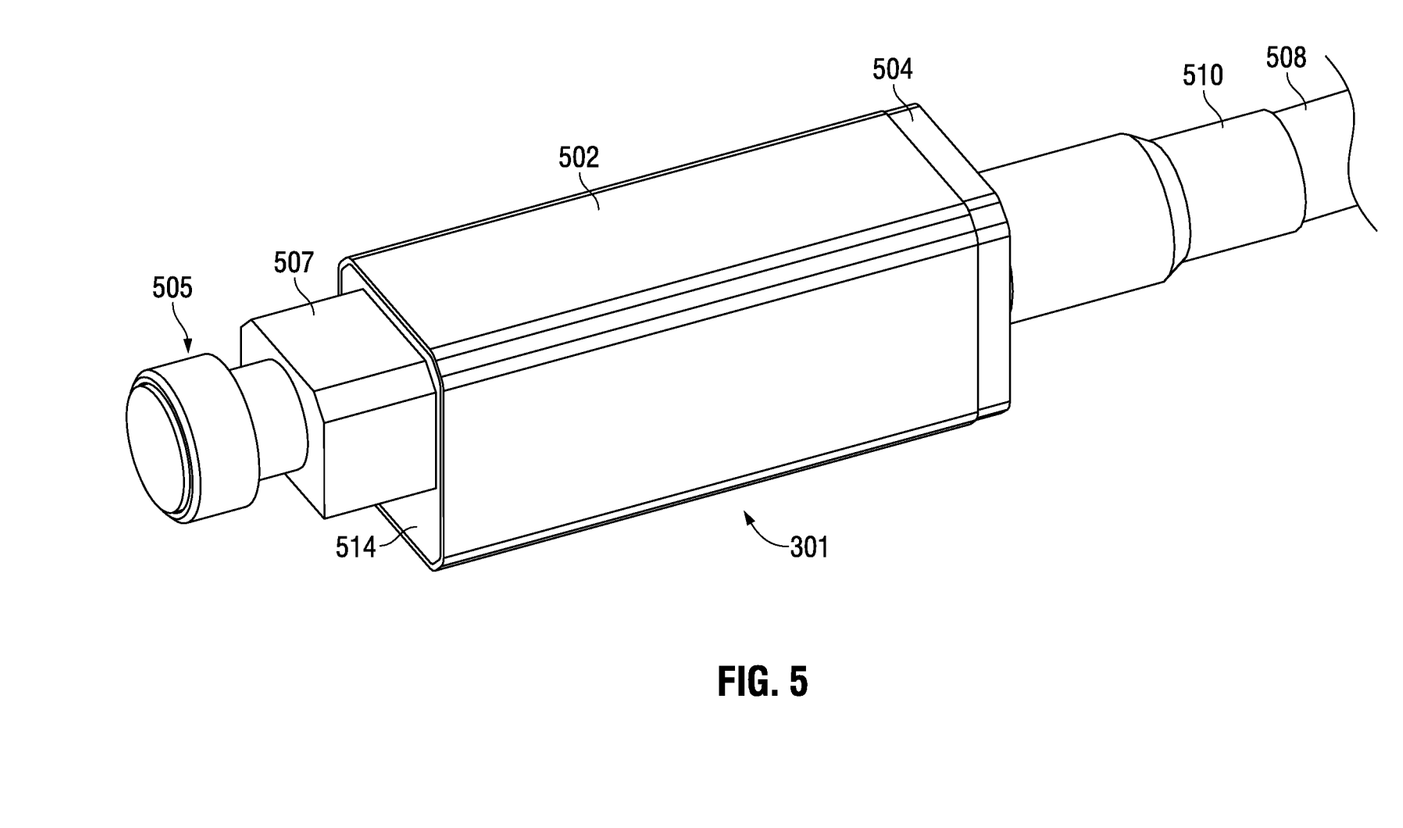
FIG. 5 is a view in perspective of the image sensor module of FIG. 3 removed from the distal head.
Figure 6:
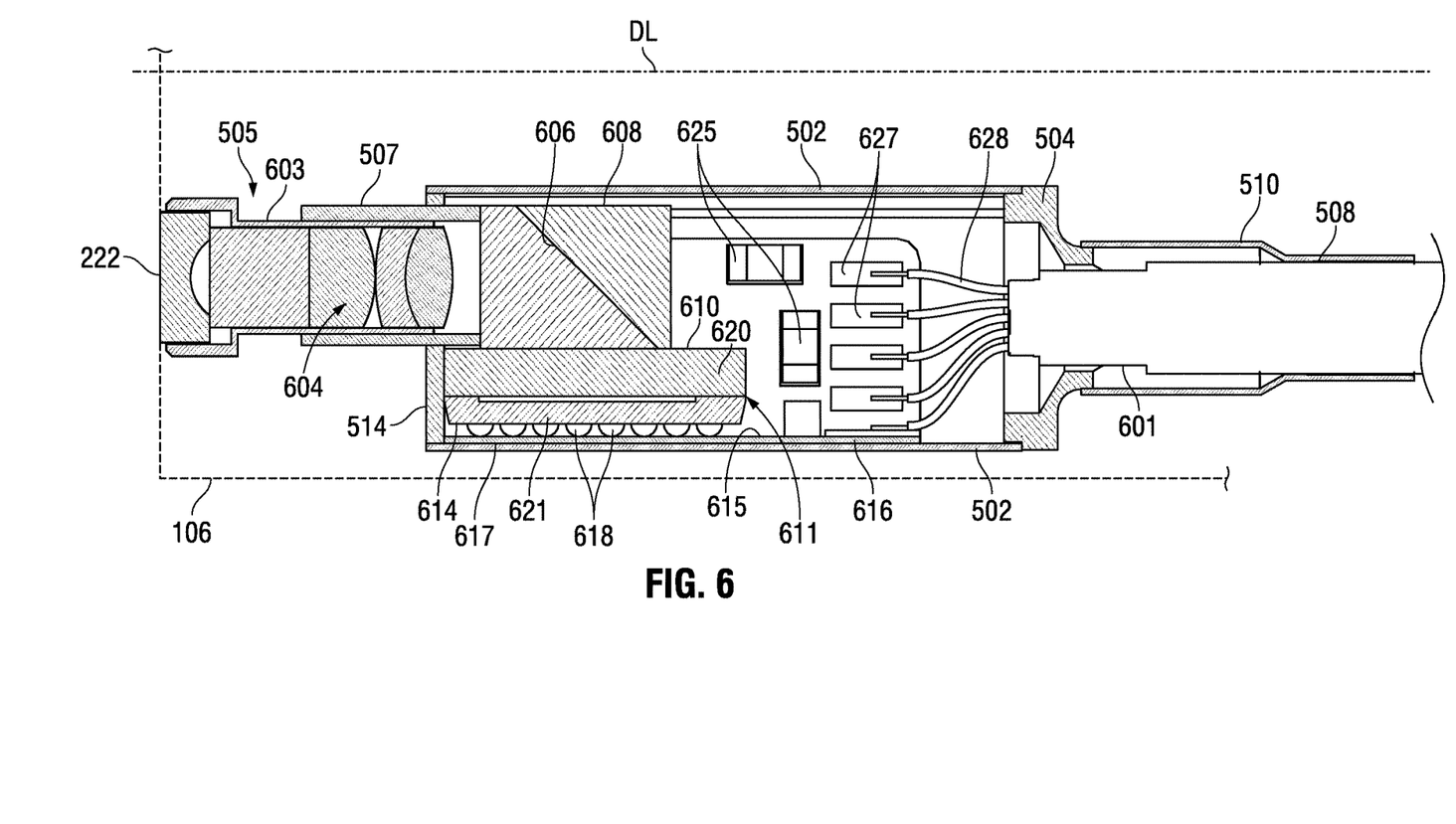
FIG. 6 is a view in section taken along line 6-6 in FIG. 5, and showing a portion of the outer surface of the distal head in phantom lines.

Referring now to FIGS. 5 and 6, image sensor module 301 includes a housing 502 connected to a cable end cap 504 at one end (the right end in the orientation of FIG. 5) and a lens assembly 505 and prism carrier 507 at the other end. A cable 508 (which may be an end portion of cable 108 in FIG. 1, or a cable connected to cable 108) is received in end cap 504 and the junction between the two is covered in this example with a heat shrink cover 510. Both the housing 502 and end cap 504 may be made of a suitable RF shielding material such as a suitable metal (stainless steel for example) and may be sealed together such as by welding about the periphery of the end of housing 502. As shown in the section view of FIG. 6, end cap 504 is in electrical contact with a shielding layer 601 of cable 508. In alternate implementations end cap 504 may be formed from a nonconductive material such as PEEK or other suitable plastic. In these implementations housing 502 may comprise a conductive metal or may be formed from a nonconductive material such as a suitable plastic. Regardless of whether housing 502 is configured to provide RF shielding, at the opposite end of housing 502, the end to the left in FIGS. 5 and 6, the housing is connected to prism carrier 507 via a layer of suitable adhesive 514 which provides a seal to the interior of image sensor module 301 at that end.

As shown in the section view of FIG. 6, lens assembly 505 includes a lens barrel 603 which carries, in this example embodiment, a number of lenses indicated generally at arrow 604. Lens assembly 505 terminates to the left in the orientation of FIG. 6 at lens 222 which is visible in the views of FIGS. 2 and 3. Lenses 604 function to focus the image received at the outer end of distal head 106 (in FIGS. 1-3) on to the angled surface 606 of turning prism 608. Prism carrier 507 receives the inner end (the right end in FIG. 6) of lens barrel 603 and positions the lens barrel relative to prism 608 which includes a transparent section to the left of angled surface 606 in FIG. 6. The image incident on the surface 606 of prism 608 is reflected downwardly in the orientation of FIG. 6 toward the top plane 610 of image sensor 611 which is operatively mounted at its bottom plane 614 to an inner face 615 of a circuit board 616 via solder balls 618 of the image sensor. Although not shown in the figures, those skilled in the art will appreciate that solder balls 618 of image sensor 611 contact corresponding contact pads on the inner face 615 of circuit board 616. The illustrated image sensor 611 comprises a chip scale package device having a cover element 620 over the semiconductor substrate (not shown separately) in a lower portion 621 of the image sensor. Image sensor 611 may comprise a CMOS or CCD image sensor, although it will be appreciated that an image sensor module according to the various aspects of the invention is not limited to any particular solid state imaging technology.

Figure 7:
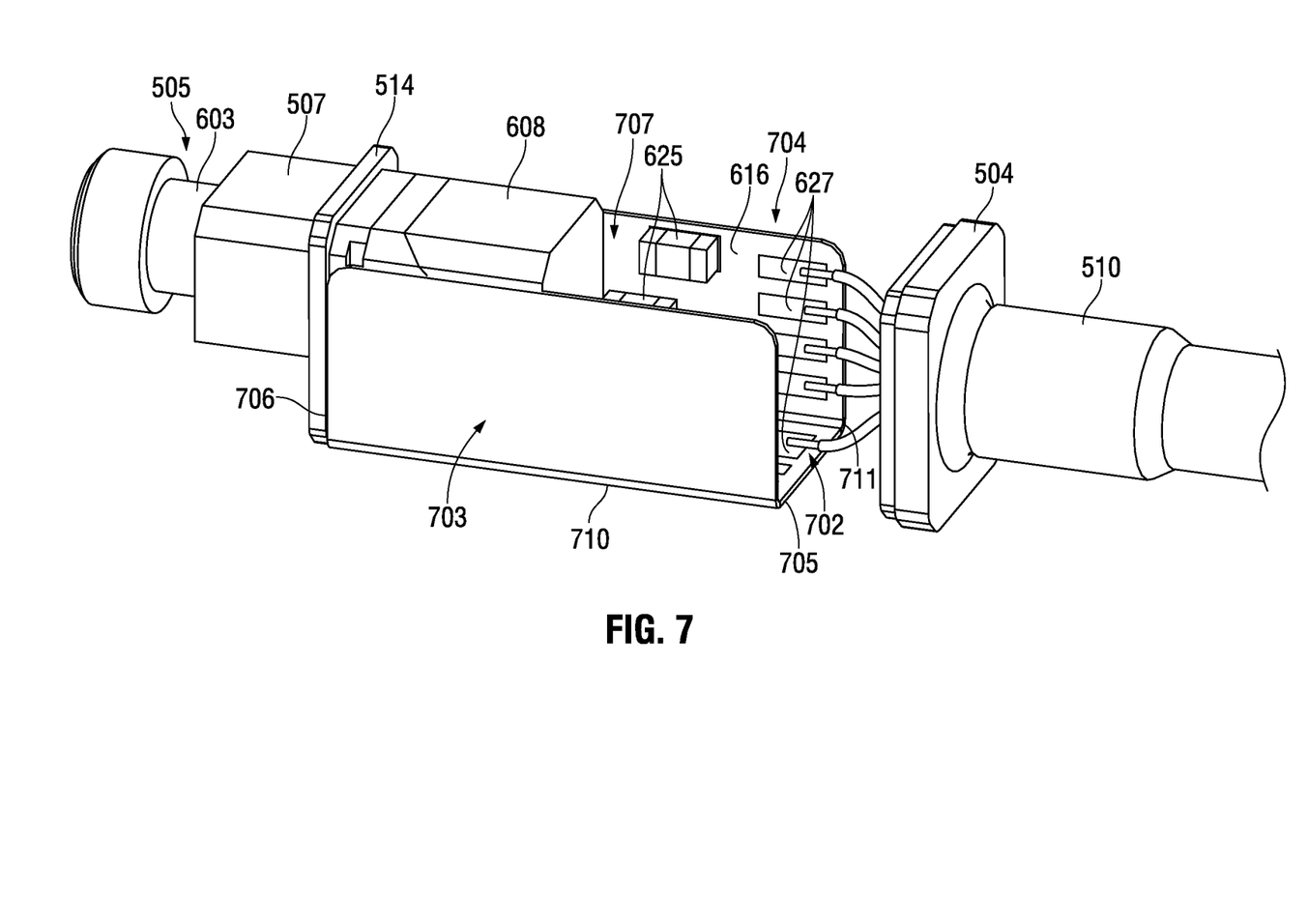
FIG. 7 is a view in perspective of the image sensor module of FIG. 5, but with the housing removed.
Figure 8:
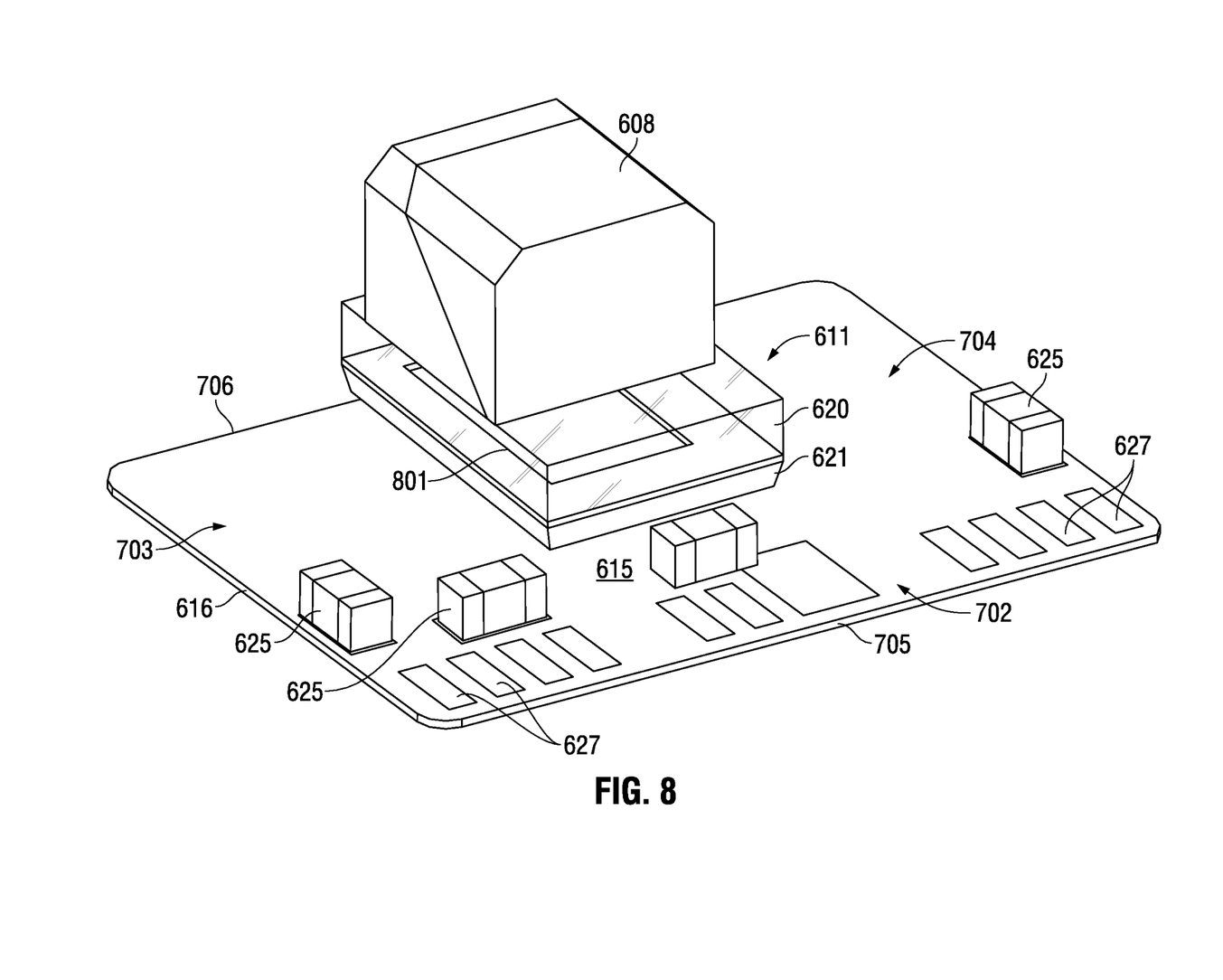
FIG. 8 is a view in perspective of the circuit board of an image sensor module prior to bending to the configuration shown in FIG. 7.

As shown best in FIG. 7 (with housing 502 removed), circuit board 616 has a center section indicated by arrow 702, a first side section shown at arrow 703, and a second side section shown at arrow 704. The various sections of circuit board 616 extend within the image sensor module from a rearward end terminating at rearward edge 705 and a forward edge terminating at forward edge 706. When configured within image module 301 (the configuration shown best in FIG. 7) first side section 703 and second side section 704 each extend in a respective plane transverse to a plane of center section 702. In this configuration, center section 702, first side section 703, and second side section 704 of circuit board 616 define a module interior volume shown generally at arrow 707 in FIG. 7 in which other components of the image sensor module are mounted. In the example implementation shown in the figures, the respective plane of first side section 703 and second side section 704 each extends approximately perpendicular to the plane of center section 702 to form a U-shape. As will be described further below, circuit board 616 includes at least areas which are flexible to accommodate bending the board into the shape shown particularly in FIG. 7. In some implementations only interface areas such as interface area 710 at the junction of first side section 703 and center section 702 and interface area 711 residing at the junction of second side section 704 and center section 702 are flexible to accommodate the required bending. In other implementations, the entire circuit board 616 may be flexible material to allow the board to be bent to the configuration shown in FIG. 7. FIG. 8 shows circuit board 616 and other components of image sensor module 301 before the circuit board has been bent to the configuration shown in FIG. 7.

As shown best in FIG. 8, image sensor 611 is mounted on inner face 615 of circuit board 616 in center section 702. In this particular embodiment a forward end of image sensor 611 is essentially flush with circuit board forward edge 706 with the image receiving surface (angled surface 606 in FIG. 6) facing in a direction from the rearward end to the forward end of circuit board 616. The rearward end of circuit board 616 extends well beyond the rearward edge of image sensor 611 leaving room on the board for an electronic component arrangement including, in this example, a number of electronic components 625. Electronic components 625 may comprise capacitors, integrated circuits, or other devices needed for proper operation of image sensor 611, all mounted on the inner face 615 of circuit board 616 so that they reside in image sensor module 301 in the module interior volume 707 defined between the various sections of the circuit board. Additionally, a number of contact pads 627 are also formed on the circuit board inner face 615. In this illustrated embodiment, contact pads 627 are arranged side-by-side in a line extending along all of the sections 702, 703, and 704 of circuit board 616, and are located in an area of the board between electronic components 625 and the rearward end of the board terminating at rearward edge 705. As shown in each of FIGS. 6-8, these contact pads 627 provide electrical contact points to circuit board 616 for wires 628 of cable 508, which provide power to the board and provide signal paths for control and data signals to and from the board. It will be appreciated that only a few of the wires 628 are shown in FIGS. 6 and 7 so that the other adjacent features of the device can be shown more clearly. However, wires such as wires 628 may be connected to contact pads 627 on any or all of the circuit board sections, 702, 703 and 704.

Image sensor module 301 may be assembled by first mounting the electronic component arrangement of components 625 and image sensor 611 on circuit board inner face 615 while the circuit board is preferably in its planar condition shown in FIG. 8. Turning prism 608 may then be mounted on image sensor 611. End cap 504 may be secured to cable 508 with the various wires 628 of the cable protruding appropriately. The conductors of the various wires 628 may be soldered or otherwise securely electrically connected to contact pads 627 with circuit board 616 preferably still in the planar condition shown in FIG. 8. The conductors from cable 508 may be connected before or after components 625 and image sensor 611 and turning prism 608 are mounted on circuit board 616. Circuit board 616 is ultimately bent to the configuration shown in FIG. 7 and then housing 502 may be slid over the forward end of the board (over board edge 706) to the position shown in FIG. 6 where the end of the housing 502 on the right in the orientation of FIG. 6 may be welded or otherwise secured about its periphery at that end to the periphery of end cap 504. The pre-assembled lens assembly 505 and prism carrier 507 may then be aligned with the image receiving face 606 of turning prism 608 as shown particularly in FIGS. 6 and 7. Sealant 514 may then be applied at the left end (in the orientation of the figures) of 502 to complete the module. Once the module is assembled as shown in FIG. 5, the module may be inserted in the image module receiving cavity 408 (shown best in FIG. 4) provided in distal section 204 in preparation for assembling the distal head components and ultimately connecting the distal head to the distal end of shaft 101 shown in FIG. 1. It will be noted that the proper registry of the protruding portion of prism carrier 507 with end section 410 of cavity 408 forces image sensor module to be inserted in a particular orientation within the distal head 106 as indicated in FIG. 6.

The configuration of image sensor module 301 with image sensor 611 (and most of turning prism 608), electronic components 625 and contact pads 627 mounted or located within the module interior volume 707 defined by the different sections 702, 703, and 704 of circuit board 616 as shown in the figures, allows the module to be compact with reduced cross-sectional dimension and minimum length. Also, the placement of image sensor module 301 in distal head 106 as shown particularly in FIG. 3, leaves maximum room for the other components received in the distal head, namely, the illumination devices and working channel shown in FIGS. 2 and 3. It may be particularly noted from FIG. 6 that image sensor module 301 is preferably mounted in distal head 106 so that the circuit board outer face 617 in the center section (702 in FIGS. 7 and 8) is located relatively closer to the nearest outer surface of the distal head (shown by the phantom line in FIG. 6) than to the central longitudinal axis DL. This preferred arrangement maximizes the space left in distal head 106 for the other components located there.

Implementations of an image sensor module according to aspects of the present invention may include an image sensor which provides an image in a widescreen aspect ratio such as 16:9 or some other ratio having one side significantly longer than the other. An image sensor module according to the present invention may accommodate such image sensors by orienting the long side in the distal head assembly running parallel to the longitudinal axis of the distal head. This is the case in the illustrated example as shown by the elongated aperture of image sensor 611 shown in the view of FIG. 8. This orientation of the image sensor 611 facilitates the orientation of image sensor module 301 shown in the figures, especially FIG. 6, with the circuit board outer face 617 very near one side of the assembled distal head 106, and relatively much further from the distal head center longitudinal axis DL.

Numerous variations in an image sensor module are possible within the scope of the present invention. For example, although circuit board 616 is flexible at least in certain areas to facilitate bending the board from the planar state shown in FIG. 8 to the final stated shown best in FIG. 7, other implementations may include rigid circuit board sections assembled into the U-shape shown in FIG. 7. Also, although light guide 212 is shown as providing illumination in the assembly of FIGS. 2 and 3, any suitable illumination device or devices may be used in a distal head incorporating an image sensor module according to the present invention. A distal head incorporating an image sensor module according to the present invention also need not include a working channel, although the compact nature of the present image sensor modules facilitate the inclusion of a working channel without making the cross-sectional dimension of the distal head too large.

As used herein, whether in the above description or the following claims, the terms "comprising," "including," "carrying," "having," "containing," "involving," and the like are to be understood to be open-ended, that is, to mean including but not limited to. Also, it should be understood that the terms "about," "substantially," and like terms used herein when referring to a dimension or characteristic of a component indicate that the described dimension/characteristic is not a strict boundary or parameter and does not exclude variations therefrom that are functionally similar. At a minimum, such references that include a numerical parameter would include variations that, using mathematical and industrial principles accepted in the art (e.g., rounding, measurement or other systematic errors, manufacturing tolerances, etc.), would not vary the least significant digit.

Any use of ordinal terms such as "first," "second," "third," etc., in the following claims to modify a claim element does not by itself connote any priority, precedence, or order of one claim element over another, or the temporal order in which acts of a method are performed. Rather, unless specifically stated otherwise, such ordinal terms are used merely as labels to distinguish one claim element having a certain name from another element having a same name (but for use of the ordinal term).

The term "each" may be used in the following claims for convenience in describing characteristics or features of multiple elements, and any such use of the term "each" is in the inclusive sense unless specifically stated otherwise. For example, if a claim defines two or more elements as "each" having a characteristic or feature, the use of the term "each" is not intended to exclude from the claim scope a situation having a third one of the elements which does not have the defined characteristic or feature.

The above described preferred embodiments are intended to illustrate the principles of the invention, but not to limit the scope of the invention. Various other embodiments and modifications to these preferred embodiments may be made by those skilled in the art without departing from the scope of the present invention. For example, in some instances, one or more features disclosed in connection with one embodiment can be used alone or in combination with one or more features of one or more other embodiments. More generally, the various features described herein may be used in any working combination.

The invention claimed is:

1. An image sensor module comprising:
   (a) a circuit board including a center section located between a first side section and a second side section, the first side section and the second side section each extending in a respective plane approximately perpendicular to a plane of the center section to define a module interior volume there between, the module interior volume extending from a forward edge of the circuit board and a rearward edge of the circuit board opposite the forward edge;
   (b) an image sensor having a bottom planar surface and a top planar surface, wherein the bottom planar surface is a planar surface of the image sensor that is securely mounted on an inner face of the circuit board within the module interior volume, and where the top planar surface is defined as a planar surface of the image sensor opposite the bottom planar surface;
   (c) a turning prism having a mounting surface and an image receiving surface, wherein the mounting surface is secured to the top planar surface of the image sensor within the module interior volume with the image receiving surface facing in a direction from the rearward edge of the circuit board to the forward edge of the circuit board;
   (d) an electronic component arrangement operatively mounted on the inner face of the circuit board between the image sensor and the rearward edge of the circuit board; and
   (e) a cable assembly including a number of wires entering the module interior volume, the wires being operatively connected to contacts located on the circuit board in the center section, first side section, and second side section between the electronic component arrangement and the rearward edge of the circuit board.

2. The image sensor module of claim 1 wherein the first side section and the second side section each extend transverse to the plane of the center section.

3. The image sensor module of claim 1 wherein the circuit board is flexible along the entire length and width thereof.

4. The image sensor module of claim 1 further including an RF shield housing extending at least from the forward edge of the circuit board to the rearward edge of the circuit board so as to enclose the circuit board along the entire length thereof.

5. The image sensor module of claim 4 further including:
   (a) an end cap; and
   (b) a prism carrier; and
   (c) wherein the RF shield housing includes a first end and a second end, the first end of the RF shield housing being connected to the prism carrier at a point along a longitudinal axis of the image sensor module spaced apart from the forward edge of the circuit board, and the second end of the RF shield housing being connected to the end cap at a point along the longitudinal axis of the image sensor module spaced apart from the rearward edge of the circuit board.

6. The image sensor module of claim 5 wherein:
   (a) the end cap is made of an RF shielding material sealed to the RF shield housing to provide continuous RF shielding there between; and
   (b) the end cap is electrically connected to a shielding layer of the cable assembly.

7. An observation instrument comprising:
   (a) an instrument handle;
   (b) an elongated shaft having a proximal end operatively connected to the instrument handle with one or more cables extending through the elongated shaft to an interior of the instrument handle;
   (c) a distal head connected to a distal end of the elongated shaft; and
   (d) an image sensor module included in the distal head, the image sensor module including:
      (i) a circuit board including a center section located between a first side section and a second side section, the first side section and the second side section each extending in a respective plane approximately perpendicular to a plane of the center section to define a module interior volume there between, the module interior volume extending from a forward edge of the circuit board and a rearward edge of the circuit board;
      (ii) an image sensor having a bottom planar surface and a top planar surface, wherein the bottom planar surface is defined as a planar surface of the image sensor that is securely mounted on an inner face of the circuit board within the module interior volume, and where the top planar surface is a planar surface of the image sensor opposite the bottom planar surface;
      (iii) a turning prism having a mounting surface and an image receiving surface, wherein the mounting surface is secured to the top planar surface of the image sensor within the module interior volume with the image receiving surface facing in a direction toward an outer end of the distal head;

(iv) an electronic component arrangement operatively mounted on the inner face of the circuit board between the image sensor and the rearward edge of the circuit board; and (v) wherein a number of wires of the one or more cables enter the module interior volume of the circuit board, the wires being operatively connected to contacts located on the circuit board in the center section, first side section, and second side section between the electronic component arrangement and the rearward edge of the circuit board.

8. The observation instrument of claim 7 wherein the circuit board defines an outer face opposite the inner face and wherein the image sensor module is mounted in the distal head so that the circuit board outer face in the center section lies closer to an outer surface of the distal head than a central longitudinal axis of the distal head.

9. The observation instrument of claim 7 wherein the first side section and the second side section each extend transverse to the plane of the center section.

10. The observation instrument of claim 7 wherein the circuit board is flexible along the entire length and width thereof.

11. The observation instrument of claim 7 wherein the image sensor module further includes an RF shield housing extending at least from the forward edge of the circuit board to the rearward edge of the circuit board so as to enclose the circuit board along the entire length thereof.

12. The observation instrument of claim 11 further including:
(a) an end cap; and
(b) a prism carrier; and
(c) wherein the RF shield housing includes a first end and a second end, the first end of the RF shield housing being connected to the prism carrier at a point along a longitudinal axis of the image sensor module spaced apart from the forward edge of the circuit board, and the second end of the RF shield housing being connected to the end cap at a point along the longitudinal axis of the image sensor module spaced apart from the rearward edge of the circuit board.

13. The observation instrument of claim 12 wherein:
(a) the end cap is made of an RF shielding material sealed to the RF shield housing to provide continuous RF shielding there between; and
(b) the end cap is electrically connected to a shielding layer of one of the one or more cables.

14. A distal head for an observation instrument, the distal head comprising:
(a) a distal head body having an image sensor receiving cavity there in; and
(b) an image sensor module mounted in the image sensor receiving cavity, the image sensor module including:
(i) a circuit board including a center section located between a first side section and a second side section, the first side section and the second side section each extending in a respective plane approximately perpendicular to a plane of the center section to define a module interior volume there between, the module interior volume extending from a forward edge of the circuit board and a rearward edge of the circuit board;

(ii) an image sensor having a bottom planar surface and a top planar surface, wherein the bottom planar surface is defined as a planar surface of the image sensor that is securely mounted on an inner face of the circuit board within the module interior volume, and where the top planar surface is a planar surface of the image sensor opposite the bottom planar surface;

(iii) a turning prism having a mounting surface and an image receiving surface, wherein the mounting surface is secured to the top planar surface of the image sensor within the module interior volume with the image receiving surface facing in a direction toward an outer end of the distal head body;

(iv) an electronic component arrangement operatively mounted on the inner face of the circuit board between the image sensor and the rearward edge of the circuit board; and (v) a cable assembly including a number of wires entering the module interior volume, the wires being operatively connected to contacts located on the circuit board in the center section, first side section, and second side section between the electronic component arrangement and the rearward edge of the circuit board.

15. The distal head of claim 14 wherein the circuit board defines an outer face opposite the inner face and wherein the image sensor module is mounted in the distal head so that the circuit board outer face in the center section lies closer to an outer surface of the distal head than a central longitudinal axis of the distal head.

16. The distal head of claim 14 wherein the first side section and second side section each extend transverse to the plane of the center section.

17. The distal head of claim 14 wherein the circuit board is flexible along the entire length and width thereof.

18. The distal head of claim 14 further including an RF shield housing extending at least from the forward edge of the circuit board to the rearward edge of the circuit board so as to enclose the circuit board along the entire length thereof.

19. The distal head of claim 18 further including:
(a) an end cap;
(b) a prism carrier; and
(c) wherein the RF shield housing includes a first end and a second end, the first end of the RF shield housing being connected to the prism carrier at a point along a longitudinal axis of the image sensor module spaced apart from the forward edge of the circuit board, and the second end of the RF shield housing being connected to the end cap at a point along the longitudinal axis of the image sensor module spaced apart from the rearward edge of the circuit board.

20. The image sensor module of claim 19 wherein:
(a) the end cap is made of an RF shielding material sealed to the RF shield housing to provide continuous RF shielding there between; and
(b) the end cap is electrically connected to a shielding layer of the cable assembly.

* * * * *